United States Patent [19]

Datta et al.

[11] Patent Number: 5,332,480
[45] Date of Patent: Jul. 26, 1994

[54] CAPILLARY BED ELECTROPHORESIS

[75] Inventors: Ravindra Datta; Robert A. Beardsley, both of Iowa City, Iowa

[73] Assignee: University of Iowa Research Foundation, Oakdale, Iowa

[21] Appl. No.: 78,577

[22] Filed: Jun. 16, 1993

[51] Int. Cl.$^5$ .................. G01N 27/26; G01N 27/447
[52] U.S. Cl. ........................ 204/180.1; 204/182.8; 204/299 R
[58] Field of Search ............. 204/299 R, 180.1, 182.8

[56] References Cited

U.S. PATENT DOCUMENTS

| | | | |
|---|---|---|---|
| 3,969,218 | 7/1976 | Scott | 204/299 R |
| 4,642,169 | 2/1987 | Yoshisato et al. | 204/180.1 |
| 5,045,172 | 9/1991 | Guzman | 204/299 R |

OTHER PUBLICATIONS

Norberto A. Guzman and Maria A. Trebilcock "Capillary Electrophoresis for Analytical Separation and Semi-Preparative Collection of Monoclonal Antibodies" Analytic Chimica Acta 249 (1991) 247–255.

Y. Tarnopolsky, A New Approach to Scaling Up Electrophoresis Separation Science and Technology, 28(1-3), pp. 719–731 No month available (1993).

X. Huang, Capillary Array Electrophoresis Using Laser–Excited Confocal Fluorescence Detection Analytical Chemistry, 64 pp. 967–972 Apr. (1992).

Primary Examiner—John Niebling
Assistant Examiner—John S. Starsiak, Jr.
Attorney, Agent, or Firm—Zarley, McKee, Thomte, Voorhees & Seas

[57] ABSTRACT

A capillary bed electrophoresis device for separating and collecting large-scale electrophoretic samples is disclosed. The invention relates to an improvement in the anticonvective packing and cooling system comprising a series of capillaries through which the sample and an eluent are driven by force. The sample is separated via an electrical gradient established axially within the capillaries while a coolant may be circulated intimately around the exterior of said capillaries to remove any Joule heating. The separated components are then collected at the discharge end of the capillaries. The system may be used with either continuous or batch electrophoresis devices.

20 Claims, 2 Drawing Sheets

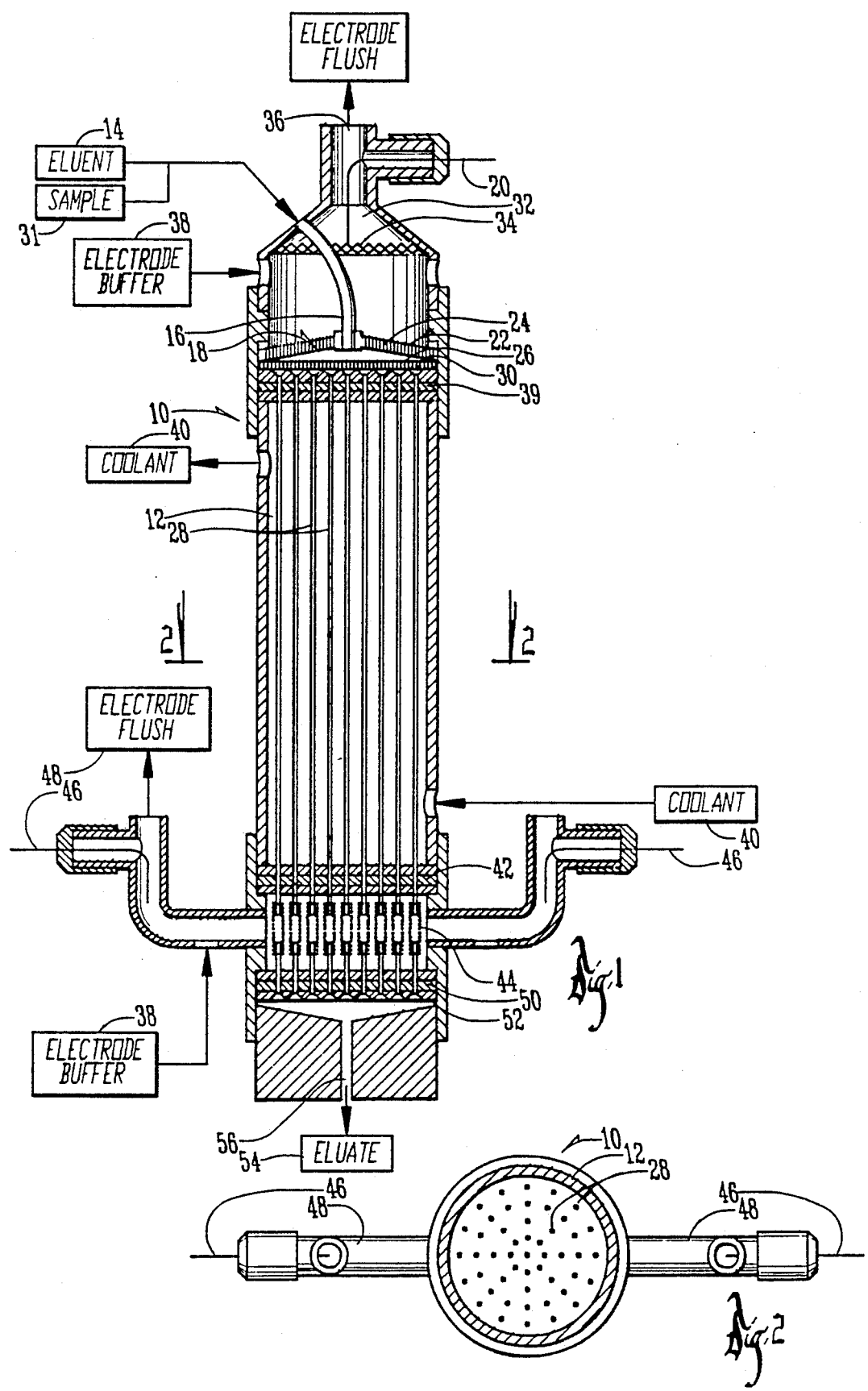

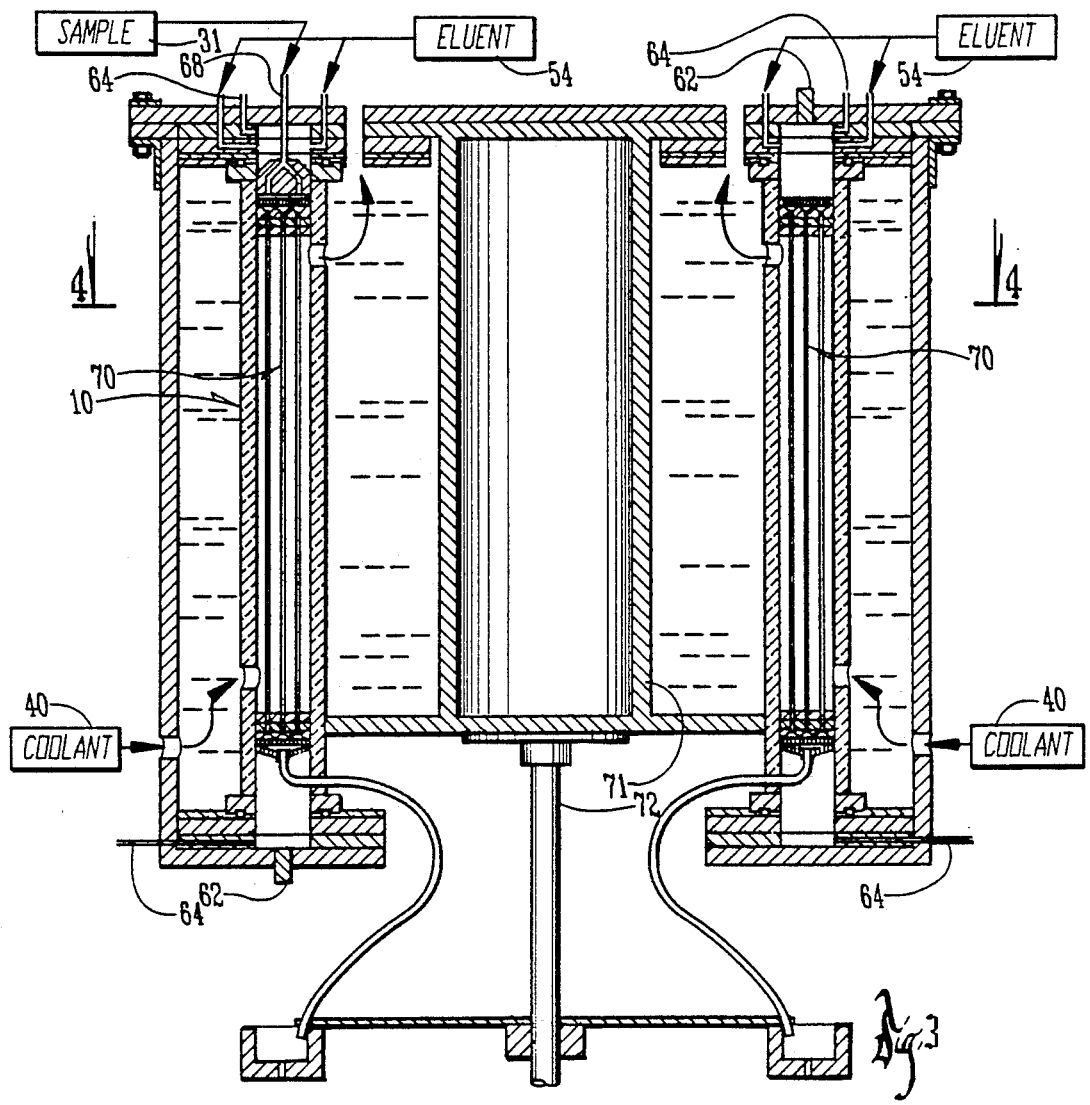
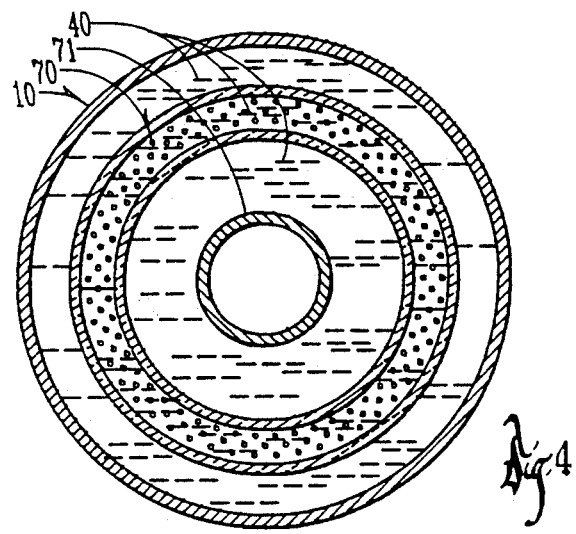

CAPILLARY BED ELECTROPHORESIS

BACKGROUND OF THE INVENTION

Electrophoresis is one of the most widely used methods for separation and purification of charged biological species. Proteins, DNA, other chemicals, cellular substructures, organelles and even whole cells have been separated by electrophoresis on an analytical, and in some cases, preparative scale. This widespread application results from the essentially universal characteristic of biological components and chemicals to acquire a charge in polar or ionic solution through ionization or ion adsorption. These charged species can then be separated from one another based on the relative differences between their migration velocities in electric field. Virtually anything that will dissolve or suspend in a conductive fluid may be seperated. Popularity electrophoresis is also due to its ability to discriminate between even closely related species. For example, analytical two dimensional electrophoresis has been shown to resolve up to 5,000 separate proteins in a single sample. This ability to separate a wide range of compounds with high selectivity suggests that a large-scale electrophoretic method would be an extremely valuable technique in downstream bioprocessing.

Promise of a powerful, relatively robust and simple bioseparation unit operation has directed many efforts towards development of large-scale methods. Thus electrophoresis could be used not only for analysis of compounds but as a large scale purification and separation device for biological species. Several fundamental characteristics of the electrophoretic process, however, have precluded the simple scale-up of batch analytical techniques. These include the Joule heating effect of the electric current, the complication of electroosmotic flow, and the dominant effect of convective dispersion in instruments larger than a critical size. The principle analytical anticonvective packings, such as porous gel, also impede heat dissipation in larger devices, limiting throughput and cannot be used for separation of many larger species, such as whole cells and organelles.

In addition, batch operation inherently reduces the possible capacity of such apparatuses. Research into large-scale electrophoresis has therefore centered almost exclusively on continuous devices utilizing no discontinuous anticonvective packing. Many such continuous devices have been proposed over the last thirty-five years. These include models with essentially no packing, freeflow) devices and other devices using packing.

One such continuous electrophoresis device is U.S. Pat. No. 4,642,169 (the Iowa Electrophoresis Column—IEC). This invention provides a continuous rotating annular electrophoresis column for separation. The electric field for this device is applied in the axial direction combined with a forced axial eluate flow through a slowly rotating annular column which is filled with anti-convective packing. By rotating the column the product path appears as helical bands each with a characteristic stationary exit point at some angular coordinate at the bottom of the column. The packing consists of spherical glass micro beads with the eluent and sample filtrating through the interstitial spaces between the beads on the basis of their electric charge. Despite this advancement in providing improved throughout the device is still plagued with the characteristic problems of packing. Traditional packing which includes gels such as polyacrylimide gel, and glass beads encounter several dispersive problems affecting the efficiency of the system for large scale separation. Thermal gradients across the device, convective dispersion due to micromixing, stream splitting and union, diffusion normal to the bulk velocity axis and effects of the device walls are all problems encountered with traditional packings.

In all current large scale electrophoresis designs, neat generated by Joule (electrical) heating is removed through one or more outer walls of the device. This results in a significant temperature gradient between the warm center of the apparatus (mid radius of an annular design such as the IEC) and the cool wall. This temperature gradient in turn creates liquid buoyancy and viscosity, voltage and chemical potential gradients across the device. In the vertical downflowing orientation involved in continuous flow designs, the difference in liquid buoyancy means that the warmer lighter eluent at the center will flow downward slower than the solvent near the wall. This results in product dispersion due to the distribution of bulk fluid velocity across the device, and can lead to destructive thermal convection. The viscosity gradient only complicates the variance in fluid velocity. The voltage gradient across the device means that the electrophoretic force and thus the electrophoretic velocity exerted on the molecule also varies across the device resulting in additional dispersion. Similarly the electroosmotic flow varies with the voltage gradient. Current attempts to alleviate thermal gradients in the electrophoresis involve circulation of a coolant around the walls of the device, in an attempt to cool and eliminate convection.

While conventional anticonvective packing, such as spherical glass beads, reduces large scale convective mixing, convective dispersion still remains. Fluid streamlines separate and mix as they pass around or through the packing, and product molecules diffuse between streamlines of different velocity and stagnant zones close to or in the packing. The pores created by interstitial spaces in the conventional packing; whether actual pores in a continuous packing, such as a gel, or whether interstitial spaces between discontinuous particles, meander through the packing and facilitate the dispersion.

And finally, due to the attempt to cool the device, the presence of device walls often leads to variation in electrophoretic environment besides those caused by thermal gradients between the vicinity of those walls and the "center of the apparatus". For example in discontinuous packing the interstitial void space increases near the walls leading to an increase in eluent velocity compared to more central regions.

It is an object of the present invention to provide a type of electrophoresis packing and cooling system which may be used with both continuous flow and batch large scale electrophoresis techniques. The system comprises a bundle of capillaries for flow of sample, which may be cooled by coolant circulated immediately around the exterior of the capillaries.

It is a further object of the invention to provide a packing for electrophoresis which will reduce and/or eliminate thermal gradients across the electrophoresis column by allowing a cooling fluid to be circulated within the column immediately around the exterior of the capillaries.

A further object of the invention is to provide a design for an electrophoresis device which will eliminate convective dispersion, radial diffusion, variations in electropotential gradient and wall effects of earlier type packing such as discontinuous packing.

A still further object of the invention is to provide an electrophoresis large scale separation device which will not be limited to merely batch separation but will also be useful for continuous flow separation.

A further object of the invention is to provide a multiple capillary bed as a replacement for discontinuous anticonvective packing and for continuous packing such as gels.

These and other objects of the invention will be more clear in the description of the invention which follows.

SUMMARY OF THE INVENTION

This invention relates to large scale electrophoresis devices which incorporate a bundle of capillaries around which a coolant may be circulated. An eluent which functions both as a solvent for the species to be separated and as an electrical conductor is driven by a pressure differential, electroosmotic flow, or other driving force through the interior of the capillaries. An electrical potential is imposed parallel to the flow through electrodes at opposite ends of the capillary bed. A coolant may be circulated through the capillary bed and around the exteriors of the capillaries to remove the head generated by the electrical current. This system may be used equally with batch electrophoresis or continuous electrophoresis devices.

BRIEF DESCRIPTION OF THE DRAWINGS

FIG. 1 is a front sectional view of one particular embodiment of this invention as applied to a batch electrophoresis device.

FIG. 2 is a cross sectional view of the batch apparatus along line 2—2 of FIG. 1.

FIG. 3 discloses a cross sectional view of another embodiment of this invention as applied to a continuous flow, rotating annular bed electrophoresis device.

FIG. 4 is a cross sectional view of the continuous flow device of FIG. 3 along line 4—4.

DETAILED DESCRIPTION OF THE INVENTION

The invention as depicted in FIG. 1 comprises an annular column electrophoresis device in which sample flow and the electrical gradient are established in the same direction. In this embodiment the capillary bed is enclosed in a housing (10) made of polycarbonate or glass encasing defining an annular chamber (12) in which the separation will take place. In the proposed column (10) an eluent (14) (for example a degassed aqueous buffer such as $KH_2PO_4$-NaOH adapted for conductivity control and biocidal action with 3% to 10% MeOH and for viscosity control with glycerol or sucrose) is fed by a pressurized feed system which may include a peristalic pump and pulse dampener, a variable area flow meter with a valve, a filter, and a eluent preparation tank. The eluent is fed through a feed tube (16) into a feed distribution zone (18) near the top of the device under the upper electrode (20). This feed distribution zone is formed between a slightly conical porous frit (22) fronted by a low MW cutoff membrane (24) and a porous frit disk (26). This allows for the electrical connection, providing for passage of the electrical current while limiting bulk flow between the upper electrode (32) and the process sections. The eluent (14) flows down through the porous frit disk (26) and enters the capillaries (28) which are a series of glass, glass-lined or polymer tubes, at the bottoms of individual conical depressions in the upper seal assembly (39). The sample (31) is injected into the eluent stream ahead of the feed distribution zone (18) by an injection means such as a high-performance liquid chromatography (HPLC) injection valve modified for electrical isolation. In an upper electrode chamber (32) bubbles are allowed to rise from the upper electrode screen (34) which distributes the electrical charge evenly across the device, and are then vented through a tube at the top (36). In addition, an electrode flush system is provided which includes a peristalic pump and pulse dampener and flow meters providing an upflowing stream of electrode buffer (38) which actively flushes electrolysis products from the upper electrode (20) and upper electrode screen through the vent (36). This flushing maintains a constant chemical and electrical environment in the electrode chamber (32) and reduces unintended pH variation in the capillary bed eluent (14). The upper seal assembly (39) around the top end of the capillaries (28) is made using a soft polymeric material compressed between two rigid polymer disks, similar to the compressed O-ring seal used in high-pressure rinsing of capillary electrophoresis capillaries. Below this, the main section of the capillary bed consists simply of a plurality of capillaries (28) being cooled by a co-current flow of coolant such as water (40). At the bottom end of the capillaries of the capillaries pass through another sandwich gasket (42) and enter a short section of membrane tubing (44) secured over a hairline fracture in each capillary tube. The tubing and fracture form the electrical connection to the lower electrodes (46) and yet inhibits the movement of separated components toward the lower electrodes, similar to the joints used to allow end column electrochemical detection in capillary electrophoresis.

Multiple lower electrodes (46) are necessitated by the difficulty in locating a single lower electrode along the axis of this device, combined with the desire to have as uniform electric field as possible. The electrode buffer and flush system again are facilitated at the bottom end of the tube. The higher conductivity of electrode buffer and greater current cross section also aid in achieving this electrical homogeneity. As with the upper electrode, the lower electrodes would be actively flushed (48) and include a flush recovery system. Below another sandwich gasket (50) the capillaries terminate into the column end plate (52) which has a slightly conical depression. Eluate (54) (product) exits at the column through a small hole in the center of the end plate (56) and flows through a flowthrough spectrophotometer or other detector and then can be collected for further analysis.

FIG. 2 depicts a cross top sectional view of the capillary electrophoresis column described and illustrates the capillaries (28) in parallel enclosed within the housing (10) along with the two bottom electrodes (46) and electrode flush tubes (48).

In operation sample is injected into the eluent flowing through the feed tube (16), flows down into the porous frit (26), through the frit into the conical depressions in the seal assembly (39), and into the capillaries (30). Upon entering the capillaries, the eluent (14), which functions as solvent for the species to be separated and as an electrical conductor, is driven by pressure differential through the interiors of the capillaries. The sample species will then separate along the axially imposed electrical gradient by virtue of their charge, while coolant (40) circulates around the capillaries removing any heat generated by Joule heating. The separated product species are then removed from the tubes by the pressure and collected through the small exit hole (56). Separated product species are removed as time differentiated portions of the eluate from the exit hole.

This embodiment of capillary bed electrophoresis uses a bulk fluid flow driven primarily by liquid head differential upon which electrophoretic velocities of the sample are superimposed. This is different from other capillary electrophoresis devices which typically drive fluid flow by electrosmosis and electrophoresis. The glass, glass-lined or polymer capillaries used here are generally on the order of 5 to 250 $\mu$m in diameter with 100 to 250 $\mu$m being preferred, rather than the less than 100 $\mu$m diameter in typical capillary electrophoresis.

This capillary bed system may also be used in continuous flow devices which use an electric field imposed parallel to the direction of bulk flow such as the Iowa Electrophoresis Column.

FIG. 3 is a depiction of this system as used with the continuous flow type column. Again the device is an annular column housing (10) having an upper and lower electrode electrode flush system (64), and buffer. Eluent is driven by a pressure differential through feed tubes (68) and distributed evenly across a bed of capillaries (70) for separation. The annular chamber is rotated and the structural details including the capillary tubes are symmetrical about a central axis (71). A rotational drive source (72) is operatively attached and acts to rotate the annular chamber (10) with respect to the central axis (71). Sample (31) is fed continuously through the sample feed tube (68) and applied to a small section of the bed. Coolant (40) is circulated around the capillary tubes. The sample again separates by virtue of the electrical potential created within the capillary tubes and each specific angular section of the capillary bed effectively separates a single impulse of sample. The rotation of the chamber combined with the differential velocities of the sample components causes the individual components to each have a characteristic stationary exit point at the end of the chamber at a given angular coordinate. The separated components and eluent discharge through a system of exit tubes arrayed along the center line of the annular space.

FIG. 4 depicts a cross-sectional view of the rotating apparatus, illustrating the column (10), the central axis (71), the capillaries (70) and the coolant (40) which is circulated among the capillary bed (70).

It is noted for purposes of this invention that this capillary bed design is not limited to continuous flow devices using a rotating annular column of electrophoretic capillary beds but may also be used with the continuous feed device which makes use of a stationary capillary bed and a rotating sample application and eluate collection.

It is understood that this description has included various embodiments of the invention and may be used with any electrophoretic system which include an electrical gradient and with forced sample flow in the same direction.

The capillary bed electrophoresis concept provides advantages for all types of electrophoresis systems. The capillary bed will cut down on thermal gradients by allowing a coolant to be circulated within the column in intimate association with the individual capillaries removing heat throughout the bed. This is advantageous over current systems which use an anticonvective packing and a coolant circulated around the walls of the bed. Reduction of this temperature gradient will reduce variations and viscosity buoyancy voltage and chemical potential gradients across the device causing more uniform flow rate of the sample and eluent. Additionally convective dispersion will be reduced because the sample will not have to meander through pores or interstitial spaces but is directed through an open continuous tube all oriented along the velocity access. Radial diffusion is restrained due to the solid capillary walls and there will be no wall effects due to faster flow along a larger wall opening since all capillaries will be identical.

Thus it can be seen that the invention accomplishes at least all of its objectives. Obviously many modifications and variations of the present invention are possible in light of the above teachings. It is therefore to be understood that within the scope of the appended claims the invention may be practiced otherwise than as specifically described.

What is claimed is:

1. A capillary bed device for large-scale separation and collection of components comprising: an elongated housing, defined by side walls having a first end disposed to receive a feed stream of a multi-component chemical sample and a second end disposed to discharge separated components;
  a plurality of spaced apart capillaries mounted within said housing and in fluid communication with the first end, and second end of the housing;
  a means for establishing an electrical gradient between the first and the second end of said housing and within the interior of said capillaries;
  a means for maintaining forced axial flow of an eluent through the interior of said capillaries, said eluent acting as a solvent and electrical conductor for said sample; and
  a means for feeding said sample into said housing and said capillaries.

2. The device of claim 1 further comprising a means for introducing a coolant to circulate within the housing around the exterior of said capillaries.

3. The device of claim 1 wherein said capillaries are made of glass, or are glass lined, or are made of a polymer.

4. The device of claim 1 wherein said housing is composed polycarbonate or glass.

5. The device of claim 1 wherein said capillaries are approximately 100 to 250 $\mu$m in diameter.

6. The device of claim 1 further comprising:
  a first electrode compartment formed between said first electrode and said annular housing; a first flush tube disclosed in fluid communication with said first electrode compartment thereby allowing a supply of continuous liquid stream to said first electrode compartment to continuously move gasses generated by the hydrolysis of water at said first electrode;
  a second electrode compartment formed between said second electrode and said chamber;
  a second flush tube disposed in fluid communication with second electrode compartment thereby allowing supply of a continuous liquid stream to said second electrode compartment to continuously remove gasses generated by hydrolysis of water at the second electrode.

7. The device of claim 1 wherein said annular capillaries include a seal assembly with conical end portions facilitating entry or exit of sample and eluent.

8. The device of claim 1 wherein said feeding means includes a feed distribution zone for receiving sample and distributing sample evenly into the capillaries; said feed distribution zone comprising a pair of porous disks horizontally disposed within the annular housing.

9. The device of claim 1 further comprising a collection zone at the second end of said capillaries said collection zone formed by an end plate and end frit.

10. The device of claim 1 further comprising a sealing gasket disposed at the first and second axial ends of said capillaries.

11. The device of claim 1 wherein said capillaries at the second axial end enter a section of membrane tubing secured over a hairline fracture in each capillary tube.

12. The device of claim 2 wherein said coolant is water.

13. A method of large-scale separation and collection of components by electrical charge, said method comprising:
 placing a multi-component sample in a feed receiving end of a capillary bed electrophoresis device;
 said electrophoresis device having an anticonvective packing comprising of plurality of axially disposed capillary tubes for receiving said sample;
 separating said components by their charge along an axial electrical gradient created within said tubes;
 forcing said components by bulk fluid flow of an eluent through said tubes by means of a pressure differential; and
 collecting said separated components at a sample discharge end of the capillary bed electrophoresis device.

14. The method of claim 13 further comprising the step of circulating a coolant around the exterior of said capillaries.

15. The method of claim 13 wherein said collection is by time differential portions of discharge.

16. The method of claim 13 wherein said collection is received by an annularly discrete exit point for discharge of eluent and sample along specific sections of the capillary bed in a continuous rotating annular bed electrophoresis device.

17. The method of claim 13 wherein said capillary tubes are made of glass or glass lined.

18. The method of claim 13 wherein said capillaries are 100-250 $\mu$m in diameter.

19. A capillary bed device for large-scale separation and collection of components comprising:
 an elongated housing, defined by side walls having a first end disposed to receive a feed stream of a multi-component chemical sample and a second end disposed to discharge separated components;
 a plurality of spaced apart capillaries mounted within said housing and in fluid communication with the first end, and second end of the housing;
 an upper and a lower electrode positioned to maintain an electrical gradient between the ends of said housing and within the interior of said capillaries;
 a means for establishing said electrical gradient;
 a means for maintaining forced axial flow of an eluent through the interior of said capillaries, said eluent acting as a solvent and electrical conductor for said sample; and
 a means for feeding said sample into said housing and said capillaries.

20. A method of large-scale separation and collection of components by electrical charge, said method comprising;
 placing a multi-component sample in a feed receiving end of a continuous flow rotating annular capillary bed electrophoresis device;
 said electrophoresis device having an anti-convective packing comprising a plurality of axially disposed capillary tubes for receiving said sample;
 separating said components by their charge along an axial electrical gradient maintained within said tubes;
 forcing said components through said tubes by means of a pressure differential;
 circulating a coolant around the exterior of said capillaries; and
 collecting said separated components at an annularly discrete exit point at a sample discharge end of the capillary bed electrophoresis device.

* * * * *